United States Patent
Hahnen et al.

[11] Patent Number: 5,957,923
[45] Date of Patent: *Sep. 28, 1999

[54] LOOP ELECTRODES FOR ELECTROCAUTERY PROBES FOR USE WITH A RESECTOSCOPE

[75] Inventors: Kevin F. Hahnen, Miami; Tracie L. Beideman, Pembroke Pines, both of Fla.

[73] Assignee: Symbiosis Corporation, Miami, Fla.

[ * ] Notice: This patent is subject to a terminal disclaimer.

[21] Appl. No.: 08/725,937

[22] Filed: Oct. 7, 1996

Related U.S. Application Data

[63] Continuation-in-part of application No. 08/425,386, Apr. 20, 1995, Pat. No. 5,569,244.

[51] Int. Cl.⁶ .................................................. A61B 17/39
[52] U.S. Cl. .............................................. 606/46; 606/49
[58] Field of Search .................... 606/45, 46, 49

[56] References Cited

U.S. PATENT DOCUMENTS

| | | | |
|---|---|---|---|
| 1,930,214 | 10/1933 | Wappler | 174/89 |
| 1,963,636 | 6/1934 | Wappler | 174/89 |
| 1,971,024 | 8/1934 | Wappler | 174/89 |
| 2,002,594 | 5/1935 | Wappler et al. | 174/89 |
| 2,004,559 | 6/1935 | Wappler et al. | 174/89 |
| 2,011,169 | 8/1935 | Wappler | 174/89 |
| 2,090,923 | 8/1937 | Wappler | 128/303.15 |
| 2,224,464 | 12/1940 | Wolf | 128/303.14 |
| 2,487,502 | 11/1949 | Willinsky | 128/303.14 |
| 2,815,757 | 12/1957 | Piar | 128/303.14 |
| 3,149,633 | 9/1964 | Zingale | 128/303.15 |
| 3,752,159 | 8/1973 | Wappler | 128/303.15 |
| 3,856,015 | 12/1974 | Iglesias | 128/303.15 |
| 3,939,839 | 2/1976 | Curtiss | 128/303.15 |
| 3,973,568 | 8/1976 | Iglesias | 128/303.15 |
| 3,990,456 | 11/1976 | Iglesias | 128/303.15 |
| 4,030,502 | 6/1977 | Iglesias | 128/303.15 |
| 4,060,087 | 11/1977 | Hiltebrandt et al. | |
| 4,116,198 | 9/1978 | Roos . | |
| 4,134,406 | 1/1979 | Iglesias | 128/303.15 |
| 4,149,538 | 4/1979 | Mrava et al. | 128/303.15 |
| 4,362,160 | 12/1982 | Hiltebrandt | 128/303.15 |
| 4,506,668 | 3/1985 | König | 128/303.15 |
| 4,649,917 | 3/1987 | Karasawa | 128/303.14 |
| 4,657,018 | 4/1987 | Hakky | 128/303.15 |

(List continued on next page.)

FOREIGN PATENT DOCUMENTS 3707-403  9/1987  Germany .................................. 606/46

OTHER PUBLICATIONS

Product Literature for WEDGE™; Microvasive, Boston Scientific Corporation; 2 pages.
VaporTome™ Resection Electrode Instructions for Use; Cataolg No. VE–LG; Circon ACMI; 6 pages.
Product Literature for STORZ Electrodes, Curettes, Cannulas,; 1 page.
Product Literature for Greenwald Surgical Company, Inc.; "Urological and Electrosurgical Instruments and Accessories"; 6 pages.

*Primary Examiner*—Lee Cohen
*Attorney, Agent, or Firm*—Testa, Hurwitz & Thibeault, LLP

[57] ABSTRACT

An electrocautery probe includes a distal loop electrode mounted between a pair of arms which are joined at their proximal ends to an electrode lead, and a mounting sleeve for slideably coupling the probe to the guide tube of a resectoscope. The arms are skewed from a longitudinal axis defined by the electrode lead and are covered with an insulative material which extends to the distal end of the arms and terminates in a straight edge parallel to a plane substantially perpendicular to the arms. The loop electrode is angled approximately 25°–35° proximally relative to a plane substantially perpendicular to the electrode lead. The loop electrode further defines sharp upper distal and proximal edges. A cross-section of the electrode further defines an upper surface, a leading distal surface, a lower distal surface, a lower proximal surface.

23 Claims, 4 Drawing Sheets

U.S. PATENT DOCUMENTS

| | | | |
|---|---|---|---|
| 4,726,370 | 2/1988 | Karasawa et al. | 128/303.15 |
| 4,917,082 | 4/1990 | Grossi et al. | 606/46 |
| 5,007,907 | 4/1991 | Nishigaki et al. | 606/46 |
| 5,064,424 | 11/1991 | Bitrolf | 606/46 |
| 5,080,660 | 1/1992 | Buelna . | |
| 5,088,998 | 2/1992 | Sakashita et al. | 606/46 |
| 5,196,011 | 3/1993 | Korth et al. | 606/46 |
| 5,201,741 | 4/1993 | Dulebohn | 606/113 |
| 5,318,564 | 6/1994 | Eggers | 606/47 |
| 5,324,288 | 6/1994 | Billings et al. | 606/45 |
| 5,342,357 | 8/1994 | Nardella | 606/40 |
| 5,354,296 | 10/1994 | Turkel | 606/41 |
| 5,374,188 | 12/1994 | Frank et al. | 433/32 |
| 5,376,087 | 12/1994 | Haber et al. | 606/27 |
| 5,395,312 | 3/1995 | Desai | 604/22 |
| 5,395,368 | 3/1995 | Ellman et al. | 606/45 |
| 5,423,813 | 6/1995 | Kaiser et al. | 606/46 |
| 5,569,244 | 10/1996 | Hahnen et al. . | |
| 5,749,870 | 5/1998 | Gloth et al. | 606/46 |
| 5,766,168 | 6/1998 | Mantell | 606/46 |

LOOP ELECTRODES FOR ELECTROCAUTERY PROBES FOR USE WITH A RESECTOSCOPE

This application is a continuation-in-part of U.S. Ser. No. 08/425,386, filed on Apr. 20, 1995, now U.S. Pat. No. 5,569,244, the complete disclosure of which is hereby incorporated by reference herein.

BACKGROUND OF THE INVENTION

1. Field of the Invention

This invention relates broadly to surgical instruments. More particularly, this invention relates to loop electrodes which are used in electrocautery probes with a resectoscope.

2. State of the Art

Prior art FIG. 1 shows a typical resectoscope 10 with an electrocautery probe 12. The resectoscope 10 includes a distal guide tube 14 and a proximal handle 16. A telescope 18 extending through the guide tube 14 is provided with a proximal eye piece 20 for viewing the interior of the bladder or other operative site. The cautery probe 12 has a distal electrode 22 which is mounted between a pair of arms 23, 25. The arms 23, 25 are joined at their proximal ends to an electrode lead 27 which is coupled via the handle 16 to a wire 24. The wire, in turn, is coupled to a source of cautery current (not shown). As seen in the prior art FIG. 2, a mounting sleeve 29 is provided on the probe 12 for slideably coupling it to the guide tube 14. The mounting sleeve 29 is typically located at the point where the arms 23, 25 are joined to the electrode lead 27. The handle 16 is provided with the capability of axially sliding the probe 12 and its distally mounted electrode 22 relative to the guide tube 14.

The resection procedure involves applying a cauterizing wattage to the electrode 22 and moving the electrode slowly through or over the prostate or endometrium while viewing the tissue through the scope 18. Thermal energy is applied through the electrode to the prostate or the endometrium so that tissue is excised. The resectoscope and cautery probe are also useful in other procedures for resecting the uterus, ureter, or renal pelvis.

Known electrodes for use in resectoscopes are available in many different shapes and sizes. U.S. Pat. No. 4,917,082 to Grossi et al., for example, discloses several embodiments of a "Resectoscope Electrode" including a coagulating electrode, a knife electrode, a punctate electrode, and a roller electrode, among others. Electrodes for use with resectoscopes are also widely available from Olsen Electrosurgical, Inc., Concord, Calif. They are available as blades, needles, balls, loops, spear tips, flexible wires, semi-circular wires, hooks, spatulas and blunt tips.

The loop electrode 22, which is shown in FIGS. 1 and 2 is the presently preferred type of electrode for prostatic resection because it can be used to cut and to coagulate. The disadvantage of the loop electrode is that in order to make the electrode sharp enough to cut smoothly, it must be made relatively thin with little surface area. The small surface area of the loop electrode compromises its effectiveness as a coagulating tool. Thus, in a prostatic resection procedure, 80% of the time devoted to the procedure is used to coagulate the prostate and stop it from bleeding.

An electrocautery probe solving the problems of the previous probes was disclosed in parent application U.S. Ser. No. 08/425,386 and is shown in FIGS. 3 and 4. The electrocautery probe 112 includes a distal loop electrode 122 mounted between a pair of arms 123, 125, which are joined at their proximal ends to an electrode lead 127, and a mounting sleeve 129 for slideably coupling the probe to the guide tube of a resectoscope. The arms 123, 125 extend parallel to the guide tube and are covered in an insulative material 131, 133 which further extends over an upper portion 131a, 133a of the loop electrode. The loop electrode defines a sharp distal edge 122a, a sharp proximal edge 122b, and a broad lower base surface 122c. A cross section of the electrode is defined by the lower base surface 122c, a distal surface 121a, and a proximal surface 121b. The loop electrode is angled approximately 10° proximally relative to a plane substantially perpendicular to the arms. Tests demonstrated that the electrode is 90% more effective in coagulation than the prior art-loop electrodes. It is believed that the sharp distal and proximal edges aid in cutting and focus cautery current to this effect while the relatively broad base serves to enhance coagulation.

However, it has been found that this probe configuration, when used over a long period of time, is prone to having the insulation 131, 133 around the arms of the probe degrade. Once the insulation degrades, it is technically possible for the electrode to electrically arc to the endoscope through which the probe is inserted.

SUMMARY OF THE INVENTION

It is therefore an object of the invention to provide an electrocautery probe with a loop electrode which is useful for cutting and for coagulating.

It is another of the invention to provide an electrocautery probe with a loop electrode having a relatively sharp current focusing edge.

It is also an object of the invention to provide an insulated electrocautery probe with a cutting and coagulating loop electrode which is arranged such that the insulation on the probe does not degrade.

It is another object of the invention to provide an electrocautery probe with a loop electrode which has an increased surface area for better coagulation.

Another object of the invention is to provide an electrocautery probe with a loop electrode which has two sharp edges, one for plunging and another for scything.

In accord with these objects which will be discussed in detail below, the electrocautery probe of the present invention includes a distal loop electrode mounted between a pair of arms which are joined at their proximal ends to an electrode lead, and a mounting sleeve for slideably coupling the probe to the guide tube of a resectoscope. The electrode lead defines a longitudinal axis. The arms of the electrocautery probe are covered with an insulative material which terminates in an edge perpendicular to the axis of the arms. The arms are also skewed from the axis of the electrode lead. The loop electrode is angled approximately 25°–35° proximally relative to a plane substantially perpendicular to the axis of the electrode lead. The electrode defines sharp upper distal and proximal edges. A cross-section of the electrode defines an upper surface, a leading distal surface, a lower distal surface, and a lower proximal surface. With the provided electrocautery probe the insulation on the arms does not degrade and the possibility of arcing from the electrode to the endoscope is reduced. At the same time, the cautery current is focused and can coagulate tissue as described in the parent application U.S. Ser. No. 08/425,386.

Additional objects and advantages of the invention will become apparent to those skilled in the art upon reference to the detailed description taken in conjunction with the provided Figures.

DETAILED DESCRIPTION OF THE PREFERRED EMBODIMENTS

Figure 1:
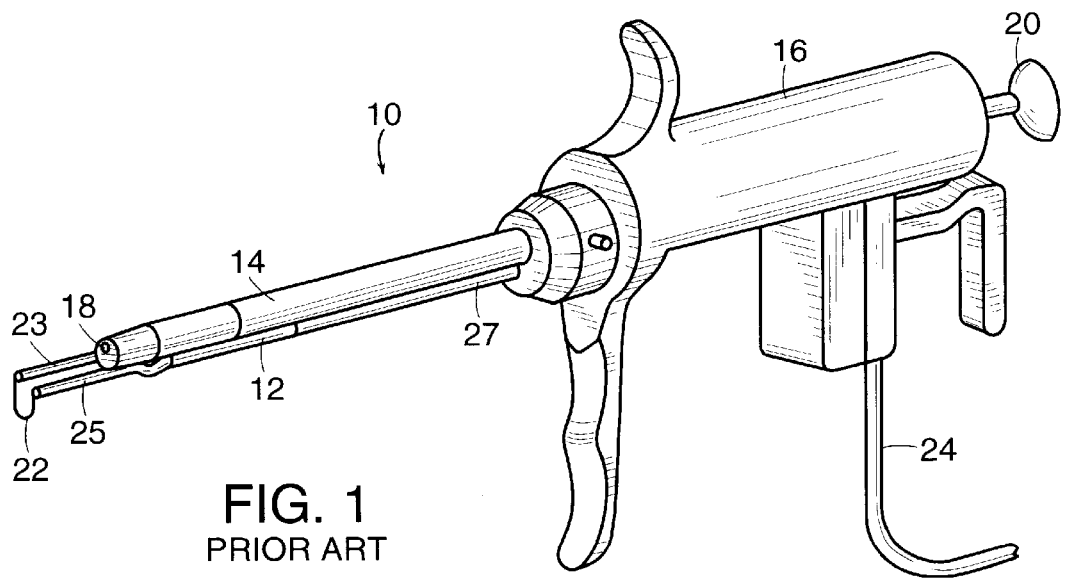
FIG. 1 is a perspective view of a prior art resectoscope with an electrocautery probe having a loop electrode.
Figure 2:
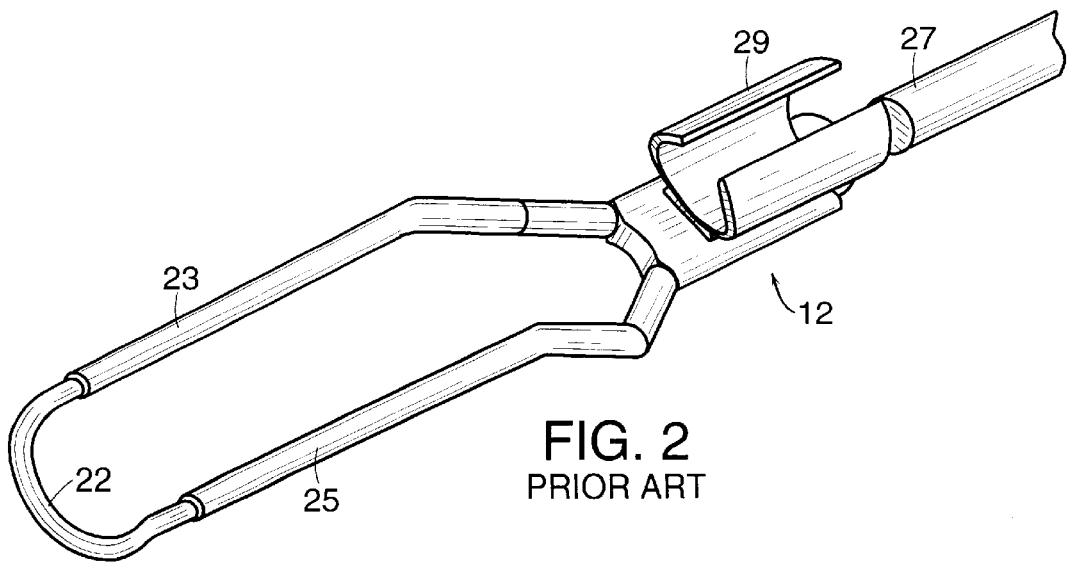
FIG. 2 is an enlarged broken perspective view of the prior art electrocautery probe of FIG. 1.
Figure 3:
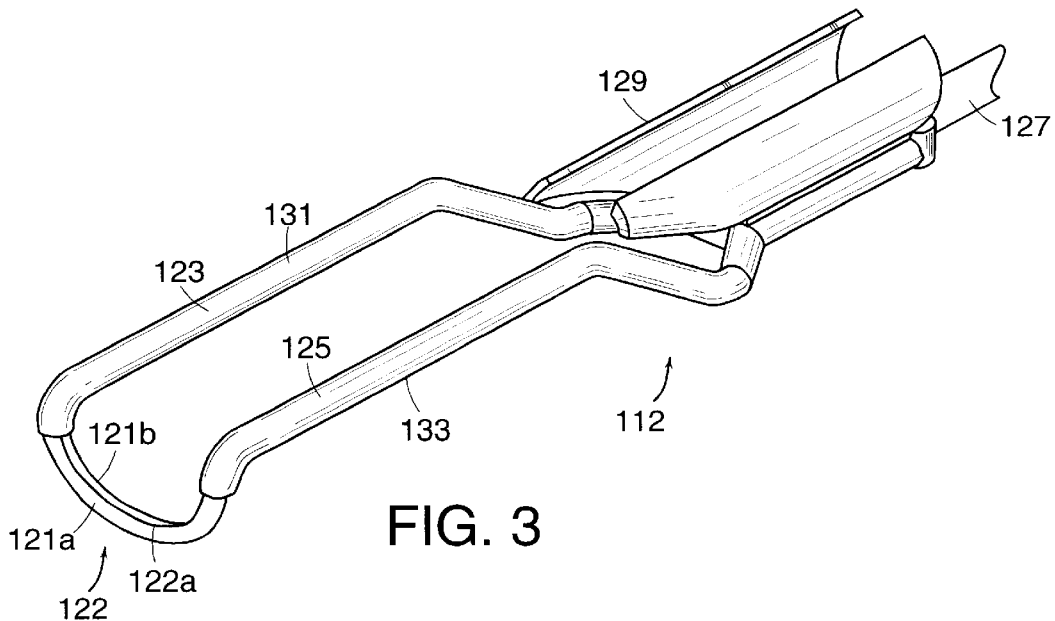
FIG. 3 is an enlarged broken perspective view of the distal end of an electrocautery probe as disclosed in the parent application.
Figure 4:
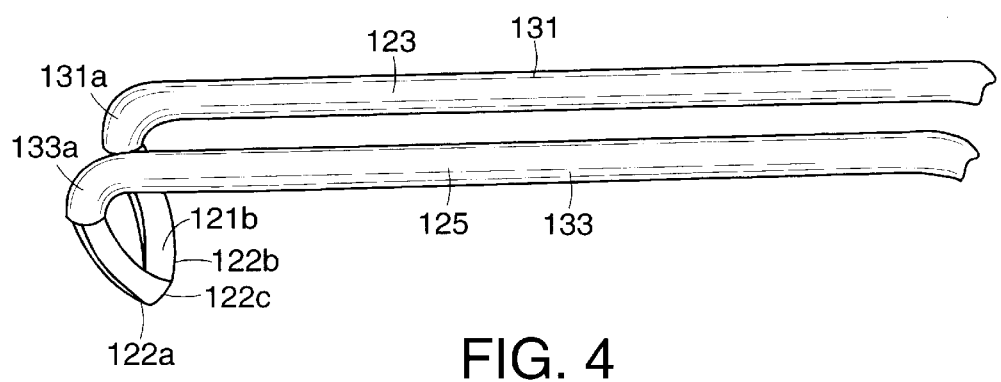
FIG. 4 is a view similar to FIG. 3 showing the proximal side of an electrode as disclosed in the parent application.
Figure 5:
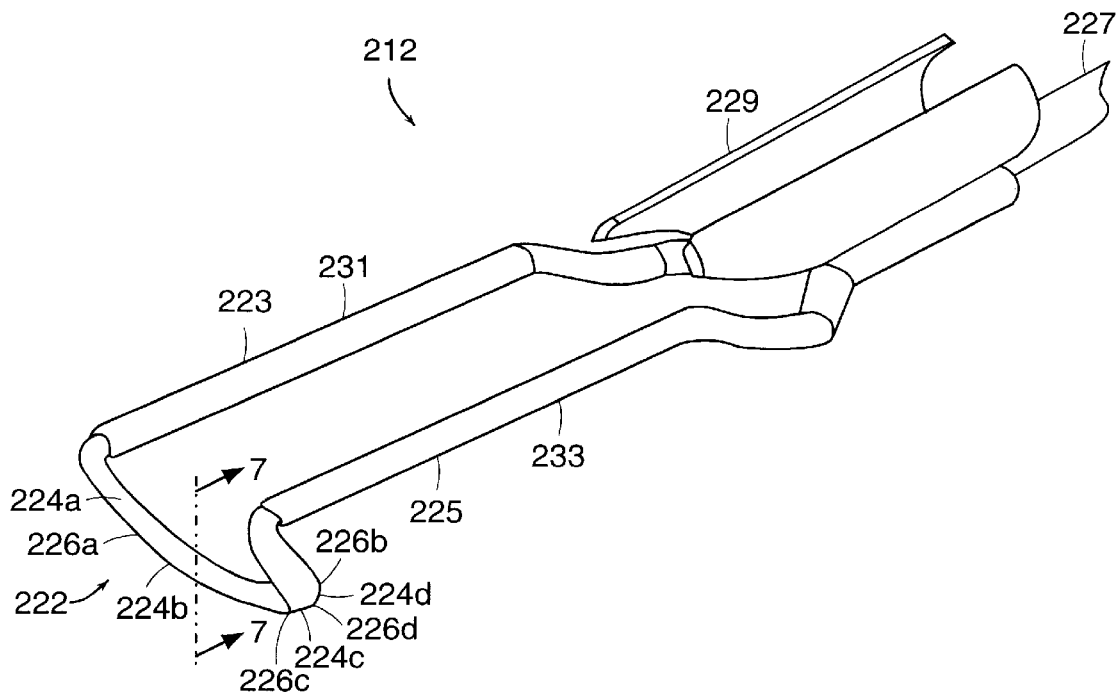
FIG. 5 is an enlarged broken perspective view of the distal end of an electrocautery probe of the invention.
Figure 7:
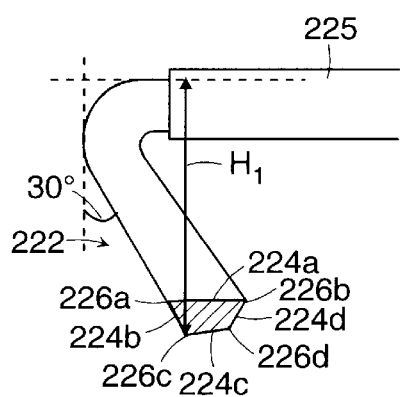
FIG. 7 is a broken cross-sectional view taken along line 7—7 in FIG. 5.
Figure 6:
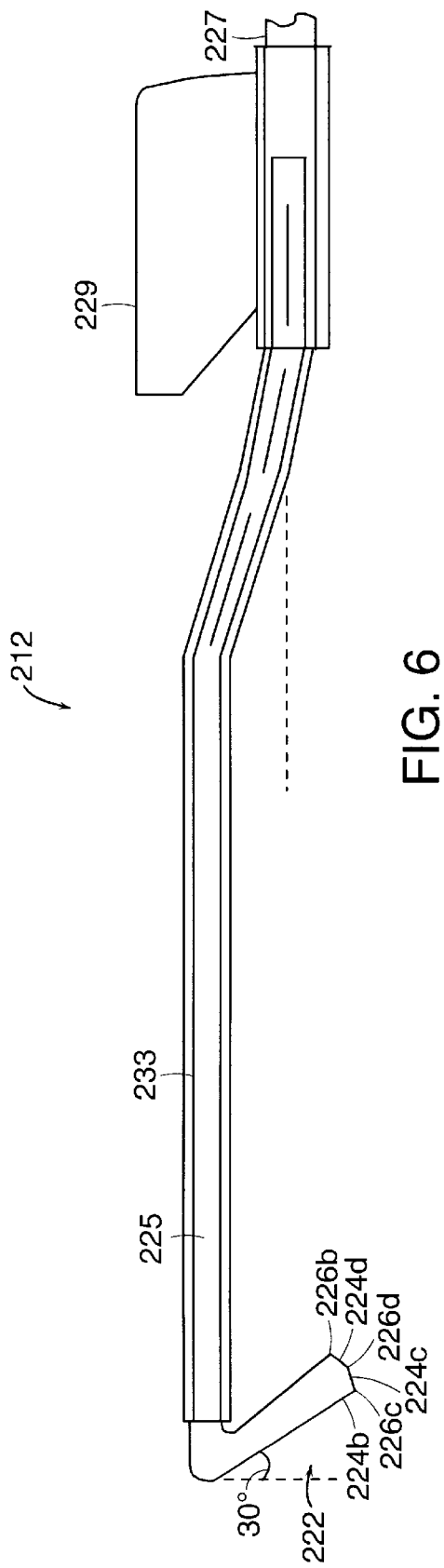
FIG. 6 is a view similar to FIG. 5 showing the proximal side of an electrocautery probe of the invention.

Referring now to FIGS. 5 through 7, a cautery probe 212 according to the invention has a distal electrode 222 which is mounted between a pair of arms 223, 225. The arms 223, 225 are joined at their proximal ends to an electrode lead 227 and a resectoscope mounting sleeve 229 is provided preferably at the location where the arms 223, 225 are joined to the electrode lead 227. The resectoscope mounting sleeve 229 is preferably made of a low dielectric material, e.g., plastic, which will reduce capacitive coupling. The electrode lead 227 defines a longitudinal axis. The arms 223, 225 extend distally and preferably angle slightly upwards, i.e., the arms skew from the longitudinal axis of the electrode lead 227. The arms 223, 225 are covered in an insulative material 231, 233, e.g., FEP, which extends over the arms to the distal ends of the arms and terminates preferably in a straight edge which is perpendicular to a plane formed by the arms. The electrode 222 is a substantially U-shaped loop coupled by its upper ends to the distal ends of the arms 223, 225. The U-shaped loop is angled approximately between 25°–35°, and preferably 30°, proximally relative to a plane substantially perpendicular to the longitudinal axis of the electrode lead 227.

The geometry of the electrode loop defines a plurality of edges. The edges include a substantially sharp upper distal edge 226a, a substantially sharp upper proximal edge 226b, a lower distal edge 226c, and a lower proximal edge 226d. A cross-section of the electrode loop defines a plurality of surfaces seen best in FIG. 7. The surfaces include a broad upper surface 224a, a leading distal surface 224b, a lower distal surface 224c, and a proximal surface 224d. The broad upper surface 224a defines a plane substantially parallel to the longitudinal axis of the electrode lead 227.

According to a presently preferred embodiment of the invention, the broad upper surface 224a of the loop electrode is approximately 0.043–0.061 inches wide, the leading distal-surface 224b extends approximately 0.014–0.018 inches from the upper surface 224a, and the lower distal surface 224c extends approximately 0.024–0.032 inches from the leading distal surface 224b to the proximal surface 224d. The electrode thereby defines a sharp upper distal edge 226a having an angle of approximately between 55°–65°, a sharp upper proximal edge 226b having an angle of approximately 42°–52°, a lower distal edge 226c having an angle of approximately 95°–105°, and a lower proximal edge 226d having an angle of approximately 135°–150°. In the presently preferred embodiment, the electrode 222 is coupled to the arms 223, 225 so that the upper distal surface 224a of the electrode lies in a plane which is angled approximately 30° proximally relative to a plane substantially perpendicular to the longitudinal axis of the electrode lead 227. The height $H_1$ of the electrode 222 from the lower distal edge 226c to the distal end of the arms 225 is approximately 0.180–0.375 inches. The electrode is preferably made of chromium cobalt or carbonless stainless steel. Tests of this electrode demonstrated superior cutting and coagulation as compared to the prior art loop electrodes. It should be noted that the sharp upper distal edge 226a and the sharp upper proximal edge 226b need not be (and preferably are not) "cutting sharp". The electrode cuts with the assistance of the cautery current passing through it. It is believed that the sharp edges provide well-defined lines of focus for the cautery current and thereby improve the cutting ability of the electrode.

Observation has shown that the preferred configuration with the 25°–35° proximal angle prevents the insulation on the arms from degrading, and thereby eliminates the possibility of arcing. In addition, the termination of the insulation in a straight edge reduces the stress placed on the insulation, and promotes longevity in the integrity of the insulation. Furthermore, the configuration maintains the superior cutting and coagulating abilities demonstrated by the loop electrode in the parent application.

There have been described and illustrated herein of a loop electrode of an electrocautery probe. While a preferred embodiment of the invention has been described, it is not intended that the invention be limited thereto, as it is intended that the invention be as broad in scope as the art will allow and that the specification be read likewise. Thus, while particular dimensions and materials have been disclosed, it will be appreciated that other dimensions and materials could be utilized. Also, while a particular electrocautery probe has been shown in connection with the electrode, it will be recognized that other types of probes could be used with similar results obtained. Moreover, while the electrode and probe have been disclosed as having particular utility in connection with a resectoscope, it will be understood that desirable results can be achieved by the electrode without the use of a resectoscope. It will therefore be appreciated by those skilled in the art that yet other modifications could be made to the provided invention without deviating from its spirit and scope as so claimed.

We claim:

1. A loop electrode for use in an electrocautery probe having two arms between which said electrode is mounted, said electrode comprising:

a substantially U-shaped conductive member angled proximally relative to a plane substantially perpendicular to a longitudinal axis of the electrocautery probe, the conductive member having a cross section defining a broad lower surface edge.

2. A loop electrode according to claim 1, wherein:

said cross section further defines an upper surface, a leading distal surface, a lower distal surface and a proximal surface.

3. A loop electrode according to claim 2, wherein:

said lower distal and proximal surfaces form a lower proximal edge having an obtuse angle, and said leading distal surface and said lower distal surface form a lower distal edge.

4. A loop electrode according to claim 3, wherein:

said lower distal edge has an angle of approximately 95°–105°, and said lower proximal edge has an angle of approximately 135°–150°.

5. A loop electrode according to claim 3, wherein:
said upper surface has a length of approximately 0.043–0.061 inches.

6. A loop electrode according to claim 5, wherein:
said leading distal surface extends approximately 0.018–0.022 inches between said upper surface and said lower distal surface, and said lower distal surface extends approximately 0.024–0.032 inches between said leading distal surface and said proximal surface.

7. A loop electrode according to claim 1, wherein:
said cross section defines a sharp upper distal edge and a sharp upper proximal edge.

8. A loop electrode according to claim 7, wherein:
said upper distal edge has an angle of approximately between 55°–65°, and said upper proximal edge has an angle of approximately 42°–52°.

9. A loop electrode according to claim 1, wherein:
said U-shaped conductive member has a height approximately 0.180–0.220 inches.

10. The loop electrode of claim 1, wherein the conductive member is angled approximately 25° to 35° proximally relative to the plane substantially perpendicular to the longitudinal axis.

11. An electrocautery probe for use with a resectoscope, comprising:
   a) a pair of conductive arms having proximal and distal ends, said arms joined together at their proximal ends;
   b) an electrode lead coupled to said proximal ends of said conductive arms and extending proximally therefrom, said electrode lead defining a longitudinal axis; and
   c) a substantially U-shaped electrode angled proximally relative to a plane substantially perpendicular to the longitudinal axis, the electrode having two upper ends, each of which is coupled to a respective one of said distal ends of said pair of conductive arms, said electrode having a cross section which defines a broad flat lower surface and at least one edge.

12. An electrocautery probe according to claim 11, wherein:
said arms lie in a first plane which is skewed from said axis of said electrode lead.

13. An electrocautery probe according to claim 11, wherein:
said cross section further defines an upper surface, a leading distal surface, a lower distal surface and a proximal surface.

14. An electrocautery probe according to claim 13, wherein:
said lower distal and proximal surfaces form a lower proximal edge having an obtuse angle, and said leading distal surface and said lower distal surface form a lower distal edge.

15. An electrocautery probe according to claim 14, wherein:
said lower distal edge has an angle of approximately 95°–105°, and said lower proximal edge has an angle of approximately 135°–150°.

16. An electrocautery probe according to claim 14, wherein:
said upper surface has a length of approximately 0.043–0.061 inches.

17. An electrocautery probe according to claim 16, wherein:
said leading distal surface extends approximately 0.018–0.022 inches between said upper surface and said lower distal surface, and said lower distal surface extends approximately 0.024–0.032 inches between said leading distal surface and said proximal surface.

18. An electrocautery probe according to claim 11, wherein:
said cross section defines a sharp upper distal edge and a sharp upper proximal edge.

19. An electrocautery probe according to claim 18, wherein:
said upper distal edge has an angle of approximately between 55°–65°, and said upper proximal edge has an angle of approximately 42°–52°.

20. An electrocautery probe according to claim 11, further comprising:
   d) an insulative sheath extending over said arms and terminating at said distal end of said arms in a straight edge substantially perpendicular to a plane formed by said arms.

21. An electrocautery probe according to claim 11, wherein:
said U-shaped member has a height approximately 0.180–0.220 inches.

22. An electrocautery probe according to claim 11, further comprising:
   d) a mounting sleeve for slideably coupling said probe to the resectoscope, said mounting sleeve made of a material which reduces capacitive coupling.

23. The electrocautery probe of claim 11, wherein the U-shaped electrode is angled approximately 25° to 35° proximally relative to the plane substantially perpendicular to the longitudinal axis.

* * * * *

UNITED STATES PATENT AND TRADEMARK OFFICE
CERTIFICATE OF CORRECTION

PATENT NO. : 5,957,923
DATED : September 28, 1999
INVENTORS : Hahnen et al.

It is certified that error appears in the above-identified patent and that said Letters Patent is hereby corrected as shown below:

In claim 1:
    line 1, replace "A loop electrode for use in an" with --An--;
    lines 2 and 3, delete "having two arms between which said electrode is mounted, said electrode";
    after line 3, insert --a pair of arms defining a longitudinal axis; and--;
    line 4, after "member," insert --mounted between the pair of arms, the conductive member being--;
    line 6, replace "a" with --the--;
    line 6, after "axis," delete "of the electrocautery probe";
    line 8, after "surface," insert --and at least one--.

In claim 2, line 1, replace "A loop electrode" with --An electrocautery probe--.

In claim 3, line 1, replace "A loop electrode" with --An electrocautery probe--.

In claim 4, line 1, replace "A loop electrode" with --An electrocautery probe--.

In claim 5, line 1, replace "A loop electrode" with --An electrocautery probe--.

In claim 6, line 1, replace "A loop electrode" with --An electrocautery probe--.

In claim 7, line 1, replace "A loop electrode" with --An electrocautery probe--.

UNITED STATES PATENT AND TRADEMARK OFFICE
CERTIFICATE OF CORRECTION

PATENT NO. : 5,957,923
DATED : September 28, 1999
INVENTOR(S) : Hahnen et al.

It is certified that error appears in the above-identified patent and that said Letters Patent is hereby corrected as shown below:

In claim 8, line 1, replace "A loop electrode" with --An electrocautery probe--.

In claim 9, line 1, replace "A loop electrode" with --An electrocautery probe--.

In claim 10, line 1, replace " The loop electrode" with --An electrocautery probe--.

Signed and Sealed this

Sixth Day of June, 2000

Q. TODD DICKINSON

Attest:

Attesting Officer

Director of Patents and Trademarks